(12) United States Patent
Frey et al.

(10) Patent No.: US 7,265,252 B1
(45) Date of Patent: Sep. 4, 2007

(54) PROCESS FOR XYLENE PRODUCTION

(75) Inventors: Stanley J. Frey, Palatine, IL (US);
Suheil F. Abdo, Lincolnshire, IL (US);
Antoine Negiz, Wilmette, IL (US);
Edwin P. Boldingh, Arlington Heights, IL (US); Vasant P. Thakkar, Elk Grove Village, IL (US); Lubo Zhou, Fox River Grove, IL (US)

(73) Assignee: UOP LLC, Des Plaines, IL (US)

( * ) Notice: Subject to any disclaimer, the term of this patent is extended or adjusted under 35 U.S.C. 154(b) by 649 days.

(21) Appl. No.: 10/739,762

(22) Filed: Dec. 18, 2003

(51) Int. Cl.
*C07C 4/02* (2006.01)
*C07C 6/00* (2006.01)
*C10G 47/00* (2006.01)

(52) U.S. Cl. .................. 585/319; 585/475; 208/108
(58) Field of Classification Search ............. 585/319, 585/475; 208/108
See application file for complete search history.

(56) References Cited

U.S. PATENT DOCUMENTS 4,127,471 A    11/1978    Suggitt et al. ............. 208/60

*Primary Examiner*—Thuan Dinh Dang
(74) *Attorney, Agent, or Firm*—David J. Piasecki

(57) ABSTRACT

A process for the conversion of a hydrocarbon feedstock to produce xylene compounds. The feedstock is selectively hydrocracked and introduced into a transalkylation zone with a hydrocarbonaceous stream rich in benzene, toluene and $C_9^+$ hydrocarbons.

17 Claims, 1 Drawing Sheet

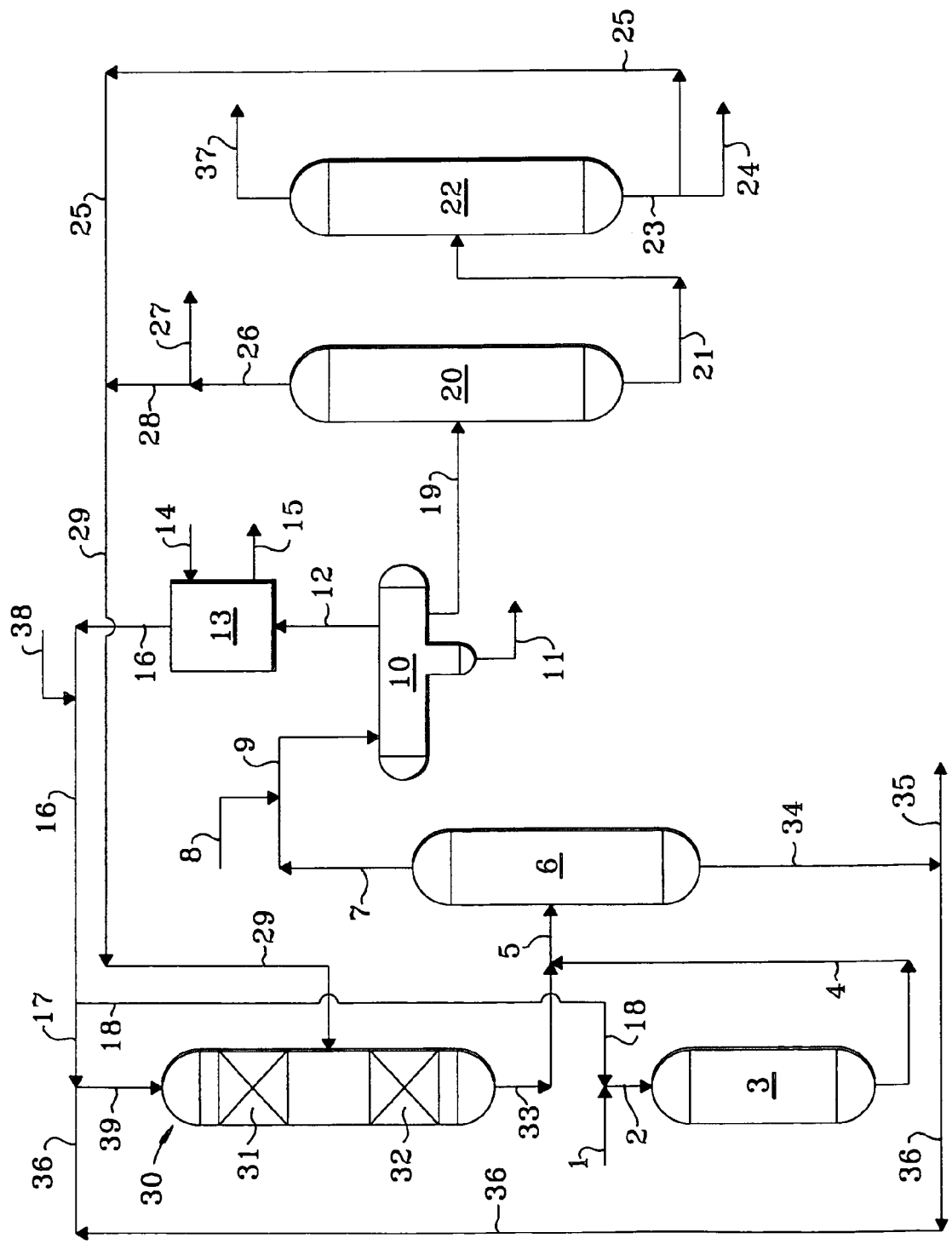

PROCESS FOR XYLENE PRODUCTION

BACKGROUND OF THE INVENTION

This invention relates to a process for the conversion of a hydrocarbon feedstock to produce xylene compounds. More specifically, the invention concerns the selective hydrocracking of aromatic compounds contained in the hydrocarbon feedstock and the immediate subsequent transalkylation of the hydrocracking zone effluent and a hydrocarbon stream rich in benzene and toluene to produce xylenes.

The xylene isomers are produced in large volumes from petroleum as feedstocks for a variety of important industrial chemicals. The most important of the xylene isomers is paraxylene, the principal feedstock for polyester which continues to enjoy a high growth rate from large base demand. Orthoxylene is used to produce phthalic anhydride, which has high-volume but mature markets. Metaxylene is used in lesser but growing volumes for such products as plasticizers, azo dyes, and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Most commonly, toluene is dealkylated to produce benzene or disproportionated to yield benzene and $C_8$ aromatics from which the individual xylene isomers are recovered. More recently, processes have been introduced to disproportionate toluene selectively to obtain higher-than-equilibrium yields of paraxylene.

A current objective of many aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. Benzene produced from disproportionation processes often is not sufficiently pure to be competitive in the market.

SUMMARY OF THE INVENTION

The present invention is a process for the production of xylene wherein a hydrocarbonaceous feedstock containing aromatic compounds is preferably introduced into a denitrification and desulfurization zone to produce an effluent which is introduced into a hot vapor-liquid product separator along with a hereinafter described transalkylation zone effluent to produce a vaporous stream comprising hydrogen, hydrogen sulfide, ammonia and $C_8^-$ aromatic hydrocarbons, and a first liquid hydrocarbonaceous stream comprising $C_9^+$ hydrocarbons. The vaporous stream is partially condensed to recover hydrogen, reject hydrogen sulfide and ammonia and to fractionate the resulting liquid hydrocarbons to produce a stream containing benzene and toluene and a second liquid stream containing $C_8^+$ hydrocarbons. The first liquid hydrocarbonaceous stream containing $C_9^+$ hydrocarbons is hydrocracked to produce a hydrocracking zone effluent containing xylene compounds. The hydrocracking zone effluent comprising xylenes, at least a portion of the second liquid hydrocarbonaceous stream comprising $C_9^+$ hydrocarbons, and at least a portion of the previously produced stream containing benzene and toluene is introduced into a transalkylation zone to produce a transalkylation zone effluent which is subsequently introduced into the hereinabove described hot vapor-liquid separator.

INFORMATION DISCLOSURE

U.S. Pat. No. 4,127,471 (Suggitt et al.) discloses a process for hydrocracking a charge stock at mild cracking conditions followed by alkyl transfer typically transalkylation or disproportionation or isomerization.

BRIEF DESCRIPTION OF THE DRAWING

The drawing is a simplified process flow diagram of a preferred embodiment of the present invention. The drawing is intended to be schematically illustrative of the present invention and not to be a limitation thereof.

DETAILED DESCRIPTION OF THE INVENTION

The process of the present invention is particularly useful for the production of xylene from a hydrocarbon feedstock. Suitable hydrocarbon feedstocks boil in the range from about 149° C. (300° F.) to about 399° C. (750° F.) and preferably contain at least about 50 volume percent aromatic compounds. Particularly preferred feedstocks contain at least a portion of light cycle oil (LCO) which is a by-product of the fluid catalytic cracking (FCC) process. LCO is an economical and advantageous feedstock since it is undesirable as a finished product and contains significant quantities of sulfur, nitrogen and polynuclear aromatic compounds. Therefore, the present invention is able to convert a low-value LCO stream into valuable xylene hydrocarbon compounds.

In one preferred embodiment of the present invention the selected feedstock is first introduced into a denitrification and desulfurization reaction zone together with hydrogen at hydrotreating reaction conditions. Preferred denitrification and desulfurization reaction conditions or hydrotreating reaction conditions include a temperature from about 204° C. (400° F.) to about 482° C. (900° F.), a pressure from about 3.5 MPA (500 psig) to about 17.3 MPa (2500 psig), a liquid hourly space velocity of the fresh hydrocarbonaceous feedstock from about 0.1 $hr^{-1}$ to about 10 $hr^{-1}$ with a hydrotreating catalyst or a combination of hydrotreating catalysts.

The term "hydrotreating" as used herein refers to processes wherein a hydrogen-containing treat gas is used in the presence of suitable catalysts which are primarily active for the removal of heteroatoms, such as sulfur and nitrogen. Suitable hydrotreating catalysts for use in the present invention are any known conventional hydrotreating catalysts and include those which are comprised of at least one Group VIII metal, preferably iron, cobalt and nickel, more preferably cobalt and/or nickel and at least one Group VI metal, preferably molybdenum and tungsten, on a high surface area support material, preferably alumina. It is within the scope of the present invention that more than one type of hydrotreating catalyst be used in the same reaction vessel. The Group VI metal is typically present in an amount ranging from about 2 to about 20 weight percent, preferably from about 4 to about 12 weight percent. The Group VI metal will typically be present in an amount ranging from about 1 to about 25 weight percent, preferably from about 2 to about 25 weight percent. Typical hydrotreating temperatures range from about 204° C. (400° F.) to about 482° C.

(900° F.) with pressures from about 3.5 MPa (500 psig) to about 17.3 MPa (2500 psig), preferably from about 3.5 MPa (500 psig) to about 13.9 MPa (2000 psig).

In accordance with a preferred embodiment of the present invention the resulting effluent from the denitrification and desulfurization zone is introduced along with a hereinafter described transalkylation zone effluent into a hot vapor-liquid separator to produce a vaporous stream comprising hydrogen, hydrogen sulfide, ammonia and $C_8^-$ aromatic hydrocarbons, and a first liquid hydrocarbonaceous stream comprising $C_9^+$ hydrocarbons. The hot vapor-liquid separator is preferably operated at a temperature from about 149° C. (300° F.) to about 288° C. (550° F.) and a pressure from about 3.5 MPa (500 psig) to about 17.3 MPa (2500 psig).

At least a portion of the first liquid hydrocarbonaceous stream comprising $C_9^+$ hydrocarbons is then introduced into a hydrocracking zone. The hydrocracking zone may contain one or more beds of the same or different catalyst. In one embodiment the preferred hydrocracking catalysts utilize amorphous bases or low-level zeolite bases combined with one or more Group VIII or Group VIB metal hydrogenating components. In another embodiment, the hydrocracking zone contains a catalyst which comprises, in general, any crystalline zeolite cracking base upon which is deposited a minor proportion of a Group VIII metal hydrogenating component. Additional hydrogenating components may be selected from Group VIB for incorporation with the zeolite base. The zeolite cracking bases are sometimes referred to in the art as molecular sieves and are usually composed of silica, alumina and one or more exchangeable cations such as sodium, magnesium, calcium, rare earth metals, etc. They are further characterized by crystal pores of relatively uniform diameter between about 4 and 14 Angstroms ($10^{-10}$ meters). It is preferred to employ zeolites having a relatively high silica/alumina mole ratio between about 3 and 12. Suitable zeolites found in nature include, for example, mordenite, stilbite, heulandite, ferrierite, dachiardite, chabazite, erionite and faujasite. Suitable synthetic zeolites include, for example, the β, X, Y and L crystal types, e.g., synthetic faujasite and mordenite. The preferred zeolites are those having crystal pore diameters between about 8-12 Angstroms ($10^{-10}$ meters), wherein the silica/alumina mole ratio is about 4 to 6. A prime example of a zeolite falling in the preferred group is synthetic Y molecular sieve.

The natural occurring zeolites are normally found in a sodium form, an alkaline earth metal form, or mixed forms. The synthetic zeolites are nearly always prepared first in the sodium form. In any case, for use as a cracking base it is preferred that most or all of the original zeolitic monovalent metals be ion-exchanged with a polyvalent metal and/or with an ammonium salt followed by heating to decompose the ammonium ions associated with the zeolite, leaving in their place hydrogen ions and/or exchange sites which have actually been decationized by further removal of water. Hydrogen or "decationized" Y zeolites of this nature are more particularly described in U.S. Pat. No. 3,130,006.

Mixed polyvalent metal-hydrogen zeolites may be prepared by ion-exchanging first with an ammonium salt, then partially back exchanging with a polyvalent metal salt and then calcining. In some cases, as in the case of synthetic mordenite, the hydrogen forms can be prepared by direct acid treatment of the alkali metal zeolites. The preferred cracking bases are those which are at least about 10 percent, and preferably at least 20 percent, metal-cation-deficient, based on the initial ion-exchange capacity. A specifically desirable and stable class of zeolites are those wherein at least about 20 percent of the ion exchange capacity is satisfied by hydrogen ions.

The active metals employed in the preferred hydrocracking catalysts of the present invention as hydrogenation components are those of Group VIII, i.e., iron, cobalt, nickel, ruthenium, rhodium, palladium, osmium, iridium and platinum. In addition to these metals, other promoters may also be employed in conjunction therewith, including the metals of Group VIB, e.g., molybdenum and tungsten. The amount of hydrogenating metal in the catalyst can vary within wide ranges. Broadly speaking, any amount between about 0.05 percent and 30 percent by weight may be used. In the case of the noble metals, it is normally preferred to use about 0.05 to about 2 weight percent. The preferred method for incorporating the hydrogenating metal is to contact the zeolite base material with an aqueous solution of a suitable compound of the desired metal wherein the metal is present in a cationic form. Following the addition of the selected hydrogenating metal or metals, the resulting catalyst powder is then filtered, dried, pelleted with added lubricants, binders or the like, if desired, and calcined in air at temperatures of e.g., 371-648° C. (700-1200° F.) in order to activate the catalyst and decompose ammonium ions. Alternatively, the zeolite component may first be pelleted, followed by the addition of the hydrogenating component and activation by calcining. The foregoing catalysts may be employed in undiluted form, or the powdered zeolite catalyst may be mixed and copelleted with other relatively less active catalysts, diluents or binders such as alumina, silica gel, silica-alumina cogels, activated clays and the like in proportions ranging between 5 and 90 weight percent. These diluents may be employed as such or they may contain a minor proportion of an added hydrogenating metal such as a Group VIB and/or Group VIII metal.

Additional metal promoted hydrocracking catalysts may also be utilized in the process of the present invention which comprises, for example, aluminophosphate molecular sieves, crystalline chromosilicates and other crystalline silicates. Crystalline chromosilicates are more fully described in U.S. Pat. No. 4,363,718 (Klotz).

The hydrocracking of the hydrocarbonaceous feedstock in contact with a hydrocracking catalyst is conducted in the presence of hydrogen and preferably at hydrocracking reactor conditions which include a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 hr$^{-1}$, and a hydrogen circulation rate from about 337 normal m$^3$/m$^3$ (2000 standard cubic feet per barrel) to about 4200 normal m$^3$/m$^3$ (25000 standard cubic feet per barrel). In accordance with the present invention, the hydrocracking conditions are selected on the basis of the feedstock with the objective of maximizing the production of xylene compounds.

The resulting effluent from the hydrocracking zone is introduced into a transalkylation zone along with a hereinafter described hydrocarbonaceous stream containing benzene and toluene, and a liquid hydrocarbonaceous stream comprising $C_9^+$ hydrocarbons to enhance the production of xylene compounds. Conditions preferably employed in the transalkylation zone normally include a temperature from about 200° C. (392° F.) to about 525° C. (977° F.) and a liquid hourly space velocity in the range from about 0.2 to about 10 hr–1.

Any suitable transalkylation catalyst may be utilized in the transalkylation zone. Preferred transalkylation catalysts contain a molecular sieve and a refractory inorganic oxide. Specific examples of zeolites which can be used are the NES, MAZ, β, MEL, EUO, FER, MFS, MTT, MTW, TON, and MOR types of zeolites. The zeolites generally are prepared by crystallizing a mixture containing an alumina source, a silica source, an alkali metal source, water and a tetraalkyl ammonium compound or its precursor. The amount of zeolite present in the catalyst can vary considerably but usually is present in an amount from about 30 to 90 mass percent and preferably from about 50 to 70 mass percent of the catalyst.

A refractory binder or matrix preferably is utilized to facilitate fabrication of the transalkylation catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, zinc oxide and silica. Alumina and/or silica are preferred binders.

One suitable example of a binder or matrix component is a phosphorus-containing alumina (hereinafter referred to as aluminum phosphate) component. The phosphorus may be incorporated with the alumina in any acceptable manner known in the art. One preferred method of preparing this aluminum phosphate is that described in U.S. Pat. No. 4,629,717 which is incorporated by reference. The technique described in the '717 patent involves the gellation of a hydrosol of alumina which contains a phosphorus compound using the well known oil drop method. Generally this technique involves preparing a hydrosol by digesting aluminum in aqueous hydrochloric acid at reflux temperatures of about 80 to 105° C. The ratio of aluminum to chloride in the sol ranges from about 0.7:1 to 1.5:1 mass ratio. A phosphorus compound is now added to the sol. Preferred phosphorus compounds are phosphoric acid, phosphorous acid and ammonium phosphate. The relative amount of phosphorus and aluminum expressed in molar ratios ranges from about 1:1 to 1:100 on an elemental basis. The resulting aluminum phosphate hydrosol mixture then is gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours. The amount of phosphorus-containing alumina component present (as the oxide) in the catalyst can range from about 10 to 70 mass percent and preferably from about 30 to 50 mass percent.

The zeolite and aluminum phosphate binder are mixed and formed into particles by means well known in the art such as gellation, piling, nodulizing, marumerizing, spray drying, extrusion or any combination of these techniques. A preferred method of preparing the zeolite/aluminum phosphate support involves adding the zeolite either to an alumina sol or a phosphorus compound, forming a mixture of the alumina sol/zeolite/phosphorus compound which is now formed into particles by employing the oil drop method described above. The particles are calcined as described above to provide a support for the metal component.

The resulting effluent from the transalkylation zone is introduced into the hereinabove described hot vapor-liquid separator and is preferably joined with the effluent from the denitrification and desulfurization zone. In one embodiment of the present invention, at least a portion of the first liquid hydrocarbonaceous stream comprising $C_9^+$ hydrocarbons produced in the hot vapor-liquid separator may be directed to a diesel pool.

The vaporous stream comprising hydrogen, hydrogen sulfide, ammonia and $C_8^-$ aromatic hydrocarbons produced in the hot vapor-liquid separator is contacted with an aqueous stream and partially condensed to produce an aqueous stream containing ammonia, a hydrogen-rich gaseous stream containing hydrogen sulfide, and a liquid stream containing $C_8^+$ aromatic hydrocarbons, benzene and toluene in a cold vapor-liquid separator preferably maintained at a temperature in the range from about 38° C. (100° F.) to about 71° C. (160° F.). The hydrogen-rich gaseous stream containing hydrogen sulfide is introduced into an acid gas recovery zone which is preferably operated at essentially the same pressure as the hydrocracking zone and a temperature in the range from about 38° C. (100° F.) to about 71° C. (160° F.). A lean solvent such as an amine solution, for example, is contacted with the hydrogen-rich gaseous stream to absorb the hydrogen sulfide. Preferred amines include mono ethanol amine and di ethanol amine. A rich solvent containing absorbed hydrogen sulfide is recovered. A hydrogen-rich gaseous stream containing a reduced concentration of hydrogen sulfide is preferably utilized to supply at least a portion of the hydrogen required in the denitrification and desulfurization zone, and the hydrocracking zone. Fresh make-up hydrogen may be introduced into the process at any suitable and convenient location.

The liquid stream containing $C_8^+$ aromatic hydrocarbons, benzene and toluene recovered from the cold vapor-liquid separator is passed to a first fractionation zone to produce a hydrocarbonaceous stream comprising benzene and toluene, and a liquid hydrocarbonaceous stream comprising $C_8^+$ aromatic hydrocarbons. At least a portion of the liquid hydrocarbonaceous stream comprising $C_8^+$ aromatic hydrocarbons is passed to a second fractionation zone to produce a xylene-rich hydrocarbon product stream and a second hydrocarbonaceous stream containing $C_9^+$ hydrocarbons. At least a portion of the second hydrocarbonaceous stream containing $C_9^+$ hydrocarbons and at least a portion of the hydrocarbonaceous stream comprising benzene and toluene is introduced into the transalkylation zone as described hereinabove.

DETAILED DESCRIPTION OF THE DRAWING

In the drawing, the process of the present invention is illustrated by means of a simplified schematic flow diagram in which such details as pumps, instrumentation, heat-exchange and heat-recovery circuits, compressors and similar hardware have been deleted as being non-essential to an understanding of the techniques involved. The use of such miscellaneous equipment is well within the purview of one skilled in the art.

With reference now to the drawing, a hydrocarbonaceous feedstock containing light cycle oil is introduced into the process via line 1 and is admixed with a hydrogen-rich gaseous stream provided via line 18 and the resulting admixture is carried via line 2 and introduced into denitrification and desulfurization zone 3. An effluent stream is removed from denitrification and desulfurization zone 3 via line 4 and line 5 and introduced into hot vapor-liquid separator 6. A vaporous stream containing hydrogen, hydrogen sulfide, ammonia and $C_8^-$ aromatic hydrocarbons is removed from hot vapor-liquid separator 6 via line 7 and is contacted with an aqueous stream provided via line 8 and the resulting admixture is cooled and introduced via line 9 into cold vapor-liquid separator 10. An aqueous stream containing aqueous soluble compounds including ammonia is removed from cold vapor-liquid separator 10 via line 11 and recovered. A hydrogen-rich gaseous stream containing hydrogen sulfide is removed from cold vapor-liquid separator 10 via line 12 and introduced into acid gas scrubber 13. A lean acid gas scrubbing solution is introduced via line 14 into acid gas scrubbing zone 13 and a rich acid gas scrubbing solution containing hydrogen sulfide is removed from acid gas scrubbing zone 13 via line 15 and recovered. A hydrogen-rich gaseous stream containing a reduced concentration of hydrogen sulfide is removed from acid gas scrubbing zone 13 via line 16 and is admixed with a hydrogen make-up stream provided via line 38 and the resulting admixture is carried via line 16. A first portion of the hydrogen-rich gaseous stream carried via line 16 is carried via lines 17 and 39 and introduced into reaction zone 30 and a second portion is carried via lines 18 and 2 and introduced into denitrification and desulfurization zone 3. A liquid hydrocarbonaceous stream containing $C_9^+$ hydrocarbons is removed from hot vapor liquid separator 6 via line 34 and a portion is transported via lines 36 and 39 and introduced into reaction zone 30. Another portion of the liquid hydrocarbonaceous stream comprising $C_9^+$ hydrocarbons is removed from the process via line 35. A liquid hydrocarbonaceous stream containing $C_8^-$ aromatic hydrocarbons is removed from cold vapor-liquid separator 10 via line 19 and introduced into fractionation zone 20. A liquid hydrocarbonaceous stream containing benzene and toluene is removed from fractionation zone 20 via line 26 and a portion thereof is removed from the process via line 27 and another portion is carried via lines 28 and 29 and introduced into reaction zone 30. A liquid hydrocarbonaceous stream containing $C_8^+$ hydrocarbons is removed from fractionation zone 20 via line 21 and introduced into fractionation zone 22. A xylene-rich hydrocarbon product stream is removed from fractionation zone 22 via line 37 and recovered. A $C_9^+$ hydrocarbon stream is removed from fractionation zone 22 via line 23 and a first portion is removed from the process via line 24 and a second portion is carried via lines 25 and 29 and introduced into reaction zone 30. Reactants which were previously described as entering reaction zone 30 via line 39 flow through hydrocracking zone 31 and are admixed with a reactant stream previously described as being introduced via line 29 and the resulting admixture is introduced into transalkylation zone 32. A resulting effluent from reaction zone 30 is transported via lines 33 and 5 and introduced into hot vapor-liquid separator 6.

The foregoing description and drawing clearly illustrate the advantages encompassed by the process of the present invention and the benefits to be afforded with the use thereof.

What is claimed is:

1. A process for the production of xylene comprising
    (a) reacting a first hydrocarbonaceous stream comprising $C_9^+$ hydrocarbons in a hydrocracking zone over a hydrocracking catalyst to produce a hydrocracking zone effluent comprising xylenes;
    (b) reacting at least a portion of the hydrocracking zone effluent in a transalkylation zone over a transalkylation catalyst to produce a transalkylation zone effluent;
    (c) passing the transalkylation zone effluent into a product separator to produce a product stream and a second hydrocarbonaceous stream comprising $C_9^+$ hydrocarbons;
    (d) passing at least a portion of the second hydrocarbonaceous stream comprising $C_9^+$ hydrocarbons to the hydrocracking zone; and
    (e) recovering xylenes from the product stream produced in step (c).

2. The process of claim 1 wherein a third hydrocarbonaceous stream comprising $C_9^+$ hydrocarbons and a fourth hydrocarbonaceous stream comprising benzene and toluene are reacted in the transalkylation zone in step (b).

3. The process of claim 2 wherein at least a portion of the product stream produced in step (c) is fractionated to obtain the third hydrocarbonaceous stream and the fourth hydrocarbonaceous stream.

4. The process of claim 1 wherein the product separator is operated at a temperature from about 149° C. (300° F.) to about 288° C. (550° F.) and a pressure from about 3.5 MPa (500 psig) to about 17.3 MPa (2500 psig).

5. A process for the production of xylene comprising the steps of:
    (a) introducing a hydrocarbonaceous feedstock and a hereinafter described transalkylation zone effluent into a product separator to produce a vaporous stream comprising hydrogen, hydrogen sulfide, ammonia and $C_8^-$ aromatic hydrocarbons, and a first liquid hydrocarbonaceous stream comprising $C_9^+$ hydrocarbons;
    (b) passing at least a portion of the vaporous stream comprising hydrogen, hydrogen sulfide, ammonia and $C_8^-$ aromatic hydrocarbons to a first fractionation zone to produce a hydrocarbonaceous stream comprising benzene and toluene, and a liquid hydrocarbonaceous stream comprising $C_8^+$ aromatic hydrocarbons;
    (c) passing at least a portion of the liquid hydrocarbonaceous stream comprising $C_8^+$ aromatic hydrocarbons recovered in step (b) to a second fractionation zone to produce a xylene-rich hydrocarbon product stream and a second liquid hydrocarbonaceous stream comprising $C_9^+$ hydrocarbons;
    (d) reacting at least a portion of the first liquid hydrocarbonaceous stream comprising $C_9^+$ hydrocarbons in a hydrocracking zone to produce a hydrocracking zone effluent comprising xylenes; and
    (e) reacting at least a portion of the hydrocracking zone effluent comprising xylenes, at least a portion of the second liquid hydrocarbonaceous stream comprising $C^{9+}$ hydrocarbons produced in step (c), and at least a portion of the hydrocarbonaceous stream comprising benzene and toluene from step (b) in a transalkylation zone to produce a transalkylation zone effluent.

6. The process of claim 5 wherein the hydrocarbonaceous feedstock comprises light cycle oil.

7. The process of claim 5 wherein the product separator is operated at a temperature from about 149° C. (300° F.) to about 288° C. (550° F.) and a pressure from about 3.5 MPa (500 psig) to about 17.3 MPa (2500 psig).

8. The process of claim 5 wherein the transalkylation zone is operated at conditions including a temperature from about 200° C. (392° F.) to about 525° C. (977° F.) and a liquid hourly space velocity in the range from about 0.2 to about 10 $hr^{-1}$.

9. The process of claim 5 wherein the hydrocracking zone is operated at conditions including a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 hr$^{-1}$ and a hydrogen circulation rate from about 337 n m$^3$/m$^3$ (2000 standard cubic feet per barrel) to about 4200 n m$^3$/m$^3$ (25000 standard cubic feet per barrel).

10. A process for the production of xylene comprising the steps of:
    (a) introducing a hydrocarbonaceous feedstock into a denitrification and desulfurization zone to produce a denitrification and desulfurization zone effluent stream;
    (b) introducing the denitrification and desulfurization zone effluent stream and a hereinafter described transalkylation zone effluent into a product separator to produce a vaporous stream comprising hydrogen, hydrogen sulfide, ammonia and $C_8^-$ aromatic hydrocarbons, and a first liquid hydrocarbonaceous stream comprising $C_9^+$ hydrocarbons;
    (c) passing at least a portion of the vaporous stream comprising hydrogen, hydrogen sulfide, ammonia and $C_8^-$ aromatic hydrocarbons to a first fractionation zone to produce a hydrocarbonaceous stream comprising benzene and toluene, and a liquid hydrocarbonaceous stream comprising $C_8^+$ aromatic hydrocarbons;
    (d) passing at least a portion of the liquid hydrocarbonaceous stream comprising $C_8^+$ aromatic hydrocarbons recovered in step (c) to a second fractionation zone to produce a xylene-rich hydrocarbon product stream and a second liquid hydrocarbonaceous stream comprising $C_9^+$ hydrocarbons;
    (e) reacting at least a portion of the first liquid hydrocarbonaceous stream comprising $C_9^+$ hydrocarbons in a hydrocracking zone to produce a hydrocracking zone effluent comprising xylenes; and
    (f) reacting at least a portion of the hydrocracking zone effluent comprising xylenes, at least a portion of the second liquid hydrocarbonaceous stream comprising $C^{9+}$ hydrocarbons produced in step (d), and at least a portion of the hydrocarbonaceous stream comprising benzene and toluene from step (c) in a transalkylation zone to produce a transalkylation zone effluent.

11. The process of claim 10 wherein the hydrocarbonaceous feedstock comprises light cycle oil.

12. The process of claim 10 wherein the hydrocarbonaceous feedstock boils in the range from about 149° C. (300° F.) to about 399° C. (750° F.) and containing at least about 50 volume percent aromatic compounds.

13. The process of claim 10 wherein the denitrification and desulfurization zone is operated at conditions including a temperature from about 204° C. (400° F.) to about 482° C. (900° F.), a pressure from about 3.5 MPa (500 psig) to about 17.3 MPa (2500 psig) and a liquid hourly space velocity from about 0.1 hr$^{-1}$ to about 10 hr$^{-1}$.

14. The process of claim 10 wherein the product separator is operated at a temperature from about 149° C. (300° F.) to about 288° C. (550° F.) and a pressure from about 3.5 MPa (500 psig) to about 17.3 MPa (2500 psig).

15. The process of claim 10 wherein the transalkylation zone is operated at conditions including a temperature from about 200° C. (392° F.) to about 525° C. (977° F.) and a liquid hourly space velocity in the range from about 0.2 to about 10 hr$^{-1}$.

16. The process of claim 10 wherein the hydrocracking zone is operated at conditions including a temperature from about 232° C. (450° F.) to about 468° C. (875° F.), a pressure from about 3.5 M (500 psig) to about 20.8 MPa (3000 psig), a liquid hourly space velocity (LHSV) from about 0.1 to about 30 hr$^{-1}$ and a hydrogen circulation rate from about 337 n m$^3$/m$^3$ (2000 standard cubic feet per barrel) to about 4200 n m$^3$/m$^3$ (25000 standard cubic feet per barrel).

17. A process for the production of xylene comprising the steps of:
    (a) introducing a hydrocarbonaceous feedstock comprising light cycle oil into a denitrification and desulfurization zone to produce a denitrification and desulfurization zone effluent stream;
    (b) introducing the denitrification and desulfurization zone effluent stream and a hereinafter described transalkylation zone effluent into a product separator to produce a vaporous stream comprising hydrogen, hydrogen sulfide, ammonia and $C_8^-$ aromatic hydrocarbons, and a first liquid hydrocarbonaceous stream comprising $C_9^+$ hydrocarbons;
    (c) passing at least a portion of the vaporous stream comprising hydrogen, hydrogen sulfide, ammonia and $C_8^-$ aromatic hydrocarbons to a first fractionation zone to produce a hydrocarbonaceous stream comprising benzene and toluene, and a liquid hydrocarbonaceous stream comprising $C_8^+$ aromatic hydrocarbons;
    (d) passing at least a portion of the liquid hydrocarbonaceous stream comprising $C_8^+$ aromatic hydrocarbons recovered in step (c) to a second fractionation zone to produce a xylene-rich hydrocarbon product stream and a second liquid hydrocarbonaceous stream comprising $C_9^+$ hydrocarbons;
    (e) reacting at least a portion of the first liquid hydrocarbonaceous stream comprising $C_9^+$ hydrocarbons in a hydrocracking zone to produce a hydrocracking zone effluent comprising xylenes; and
    (f) reacting at least a portion of the hydrocracking zone effluent comprising xylenes, at least a portion of the second liquid hydrocarbonaceous stream comprising $C_9^+$ hydrocarbons produced in step (d), and at least a portion of the hydrocarbonaceous stream comprising benzene and toluene from step (c) in a transalkylation zone to produce a transalkylation zone effluent.

* * * * *